(12) United States Patent
Tiba et al.

(10) Patent No.: US 7,649,028 B2
(45) Date of Patent: Jan. 19, 2010

(54) INTERIM DENTAL DRESSING AND RESTORATIVE MATERIAL

(75) Inventors: Amer Tiba, Lake Bluff, IL (US); David G. Charlton, Gurnee, IL (US); James C. Ragain, Lafollette, TN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 37 days.

(21) Appl. No.: 11/700,970

(22) Filed: Jan. 24, 2007

(65) Prior Publication Data

US 2007/0173559 A1    Jul. 26, 2007

Related U.S. Application Data

(60) Provisional application No. 60/762,559, filed on Jan. 25, 2006.

(51) Int. Cl.
*A61K 6/083* (2006.01)
*A61C 5/08* (2006.01)

(52) U.S. Cl. .................. 523/115; 523/116; 433/222.1; 433/228.1

(58) Field of Classification Search ................ 523/115; 433/222.1
See application file for complete search history.

(56) References Cited

U.S. PATENT DOCUMENTS

| | | | | |
|---|---|---|---|---|
| 4,317,681 | A * | 3/1982 | Beede et al. | 106/810 |
| 4,872,936 | A * | 10/1989 | Engelbrecht | 156/307.3 |
| 6,001,213 | A * | 12/1999 | Liu | 156/310 |
| 6,291,593 | B1 * | 9/2001 | Cheng | 525/292 |

* cited by examiner

*Primary Examiner*—Tae H Yoon
(74) *Attorney, Agent, or Firm*—Joseph K. Hemby, Jr.; Ning Yang; Albert Churilla

(57) ABSTRACT

The invention relates to a temporary dental formulation useful as a durable, temporary restorative. The formulation changes color during mixing to assist the operator in ensuring adequacy of mixing and enhancing visualization during placement.

3 Claims, No Drawings

INTERIM DENTAL DRESSING AND RESTORATIVE MATERIAL

CROSS-REFERENCES TO RELATED APPLICATIONS

This application claims priority to U.S. Provisional application 60/762,559 filed Jan. 25, 2006.

BACKGROUND OF INVENTION

1. Field of Invention

The invention relates to a restorative dental formulation and a method of its use for the temporary replacement of tooth structure and missing dental restorations.

2. Description of the Related Art

Tooth restoration is often accomplished by filling excavated cavities with a paste material, which is subsequently compacted and shaped to conform to the original contour of the tooth. Amalgams have been routinely employed as restoratives principally because of their durability. However, the metallic color is aesthetically unappealing. Also, biological interactions of the metallic components of dental amalgams are a concern. Tooth-colored restorative composites are usually composed of glass filler particles dispersed in methacrylate-type monomer resins. Additives such as pigments, initiators and stabilizers are also sometimes added to these compositions.

Resin-based dental restoratives have been disclosed that exhibit very favorable characteristics. For example, dental resins comprising friction-reducing additives, such as polytetrafluoroethylene have been disclosed in order to reduce wear due to friction (Temin U.S. Pat. No. 4,197,234). Fellman, et al. (U.S. Pat. No. 4,433,958) disclosed the addition of fluoropolymers as solid particulate in dental restorative compositions. Angeletakis (U.S. Pat. No. 6,395,803) discloses a resin-based dental restorative that has high condensability, low volumetric shrinkage, low shrinkage stress, higher loading, lower coefficient of thermal expansion and high wear and abrasion resistance.

Dental restoratives, such as crowns and bridges, are often used to address specific dental problems, including restoring a damaged tooth to its original shape, strengthening a tooth, or for cosmetic reasons. However, permanent restoratives are often not prepared in the dentist's office but require the involvement of a dental laboratory typically remote from the dentist's office. Additionally, dental problems arise remote from complete dental facilities such as when traveling to developing nations or in military operations. In these cases temporary dental restoratives must be utilized either until a permanent restorative can be fashioned or until a visit to more complete dental facilities can be made.

Temporary crowns and bridges are typically prepared in the dental office. The materials used for temporary restoratives are generally powder/liquid form or paste/paste form. In both forms, base material and a catalyst material are provided that causes the material to harden when the two are combined.

A temporary dental restorative material is generally dispensed using a powder/liquid system, with the base and catalyst components admixed in a specific ratio. The measured and admixed contents are then directly applied to the teeth.

In paste/paste systems, materials are most often provided in bulk cartridges having multiple chambers containing the separate components. The pastes are automatically mixed through a static mixer in predetermined volume ratios and then dispensed directly onto the teeth or dispensed onto a paper pad and then placed onto the teeth using a dental instrument.

A number of temporary restorative formulations currently exist. The most common restorative (provisional) formulations are zinc oxide based and contain eugenol (ZOE) or are glass-ionomer containing cements. Typically, glass-ionomer containing formulations offer greater durability over other, non-glass-ionomer compositions (Zanata, et al 2003). Additionally, many glass-ionomer formulations offer continuous release of fluoride (Hicks, et al, 2003). ZOE formulations, however, generally do not provide fluoride. Also, residual eugenol from temporary restorations can inhibit the setting of resins used to permanently restore the teeth (Paul, et al, 1997; Fujisawa, et al, 1997; Fonseca, et al, 2005).

Although glass-ionomer formulations exist, most have polyacids, the primary active ingredient, in the liquid portion of the formulation. The result is that within a relatively short period of time the polyacids, contained in the formulations, begin to form a gel. The net result is a shortened shelf life of the products, which is typically less than 2 years.

Packaging single-use devices for the mixing and delivery of dental restorative formulations has been disclosed. Ibsen, et al (U.S. Pat. No. 4,674,980) discloses a composite system wherein resin and exciplex members are stored separate from peroxide curing agents. The components are mixed just prior to use. Shellard, et al (U.S. application publication 2004/0033466) discloses a device for mixing and dispensing single doses of mixed paste/paste restorative formulations. In the disclosure by Shellard, catalyst and base components are in separate chambers. Mixing of the contents of the two chambers compartments occurs by applying pressure to an actuator which forces the contents of the chambers into a single tube and out through a tip. However, despite current packaging and dispensing methods, a visual, easy-to-use means for determining when restorative ingredients are properly mixed and ready for use is needed.

SUMMARY OF INVENTION

An object of this invention is a long shelf-life liquid/powder temporary dental restorative that provides durable, long-term interim restorations. The temporary restorative formulation can also contain glass-ionomer.

Another object of the invention is a liquid/powder temporary dental restorative where proper mixing of ingredients is determined by visual inspection for a color change.

An additional object of the invention is a resin-containing liquid/glass-ionomer powder temporary dental restorative formulation with extended shelf life that exhibits sustained fluoride release.

DETAIL DESCRIPTION OF THE INVENTION

Typically, current formulations for temporary, durable, fluoride-containing, dental restoratives have shelf lives of less than 2 years. The current invention relates to a fluoride containing, temporary dental formulation with an extended shelf life over currently available systems. The current inventive dental formulation also provides a visual indication when the ingredients are thoroughly mixed and the formulation is ready for application to the patient.

In a preferred embodiment, the inventive formulation is divided such that the specific components are separated into either liquid or powder compartments. The components are then mixed just prior to use. Inclusion of specific components, such as the polyacids, into the powder vis-à-vis the liquid, reduces the likelihood of premature gel formation prior to use and greatly increases the shelf life to over 2 years.

The liquid components comprises the following in the percentages (weight/weight) indicated:
  a. 2-Hydroxethylmethacrylate (HEMA) (73.5%)
  b. Tri(ethylene glycol) dimethacrylate (TEGDMA) (24.5%)
  c. 2,2'-(p-Tolylimino) diethanol (p-TID) (2.0%)

The powder components include important active ingredients. Since these components are not in liquid form, the likelihood of premature gel formation prior to mixing with the liquid is greatly reduced and therefore markedly increases shelf-life to greater than 2 years. The components in the powder compartment comprises the following in the percentage (weight/weight) indicated:
  a. glass powder (90%)
  b. D-tartaric acid (5.0%)
  c. Poly(acrylic acid) (3.0%). A preferred embodiment is acrylic acid of mw 450 kDa. However acrylic acid of other mw can be utilized.
  d. Benzoyl peroxide (2.0%)

Although the above percentages are given as a preferred embodiment, other operative ratios of components can be utilized as long as the polyacids are included in the powder. Additionally, the formulation may contain other components such as components to reduce abrasion. Upon mixing, the clear liquid and white powder begin to turn yellow as the mixture's pH decreases. With further mixing, the yellow color of the mixture becomes homogeneous.

The invention also contemplates a method of using inventive formulation to for temporary, but durable, dental restorative operations. The method includes the steps of mixing the powder and liquid compartments, just prior to use. As previously noted, the liquid is normally clear, however, upon mixing with the powder, the solution begins to turn yellow. With further mixing the solution further changes until the mixture is homogenously yellow. The yellow color, therefore, is a visual signal indicating to the dentist or technician that the restorative is thoroughly mixed and ready for application to the patient. Furthermore, the yellow color aids in the proper placement of the restorative in the patient's mouth by making it easier to see where the material is being placed. However, once the material is placed in the mouth, the yellow color reverts to a more aesthetic tooth-colored shade. Use of an objective visual indicator prevents premature application of the restorative to the patient and a better and more durable restorative.

REFERENCES

1. Angeletakis, C., U.S. Pat. No. 6,395,803 issued May 28, 2002.
2. Fellman, R. P., M. J. Hurwitz, R. M. Myers and G. F. Slack., U.S. Pat. No. 4,433,958 issued Feb. 28, 1984.
3. Fujisawa S, Kadoma Y, Action of eugenol as a retarder against polymerization of methyl methacrylate by benzoyl peroxide. *Biomaterials* 18:701-3, 1997
4. Hicks, J., F. Garcia-Godoy, K. Donly and C. Flaitz. 2003. Fluoride-releasing restorative materials and secondary caries. J Calif Dent Assoc 31:229-245.
5. Ibsen, R. L., W. R. Glace, P. A. Jensen. U.S. Pat. No. 4,674,980 issued Jun. 23, 1987.
6. Temin, S. C., U.S. Pat. No. 4,197,234 issued Apr. 8, 1980.
7. Paul S J, Scharer P, Effect of provisional cements on the bond strength of various adhesive bonding systems on dentine. *J Oral Rehabil* 24:8-14, 1997.
8. Shellard, E. R., X. Xie and S. R. Higgins. 2004. U.S. Patent Application No. 2004/0033466.
9. Zanata, R. L., M. F. Navarro, S. H. Barbosa, J. R. Lauris, E. B. Franco. 2003. Clinical evaluation of three restorative materials applied in a minimal intervention caries treatment approach. J Public Health Dent 63:221-226.

Having described the invention, one of skill in the arty will appreciate in the appended claims that many modifications and variations of the present invention are possible in light of the above teachings. It is therefore, to be understood that, within the scope of the appended claims, the invention may be practices otherwise than as specifically described.

What is claimed is:

1. A dental restorative material comprising a powder containing polyacids and a liquid containing resin activator materials wherein said powder and liquid when mixed undergoes a color change, wherein said powder comprises, D-Tartaric acid at 5.0% by weight, polyacrylic acid at 3% by weight, and benzoyl peroxide at 2.0% by weight and wherein said liquid comprises 2-hydroxethylmethacrylate at 73.5% by weight, tri(ethylene glycol) dimethacrylate at 24.5% by weight and 2,2'(p-tolylimino) diethanol at 2.0% by weight.

2. The dental restorative material of claim 1, wherein said powder also contains 50-90% by weight of glass powder.

3. A method of preparing a temporary dental restorative comprising:
  a. adding together the powder and liquid components of claim 1; and
  b. mixing said powder and liquid components until the mixture turns yellow.

* * * * *